(12) United States Patent
Winiski et al.

(10) Patent No.: US 11,359,174 B2
(45) Date of Patent: Jun. 14, 2022

(54) BIOREACTOR PARADIGM FOR THE PRODUCTION OF SECONDARY EXTRA-PARTICLE HYPHAL MATRICES

(71) Applicant: Ecovative Design LLC, Green Island, NY (US)

(72) Inventors: Jacob Michael Winiski, Troy, NY (US); Peter James Mueller, Poestenkill, NY (US)

(73) Assignee: Ecovative Design LLC, Green Island, NY (US)

(*) Notice: Subject to any disclaimer, the term of this patent is extended or adjusted under 35 U.S.C. 154(b) by 252 days.

(21) Appl. No.: 16/549,757

(22) Filed: Aug. 23, 2019

(65) Prior Publication Data
US 2020/0102530 A1 Apr. 2, 2020

Related U.S. Application Data

(60) Provisional application No. 62/740,159, filed on Oct. 2, 2018.

(51) Int. Cl.
*C12M 1/16* (2006.01)
*C12M 1/00* (2006.01)
(Continued)

(52) U.S. Cl.
CPC ............ *C12M 21/16* (2013.01); *C12M 43/04* (2013.01); *C12P 1/02* (2013.01); *A01G 18/00* (2018.02); *A01H 15/00* (2013.01); *C12N 1/14* (2013.01)

(58) Field of Classification Search
CPC .......... C12M 43/04; C12M 21/16; C12P 1/02; A01G 18/00; A01H 15/00; C12N 1/14
See application file for complete search history.

(56) References Cited

U.S. PATENT DOCUMENTS

| 1,979,176 A | 10/1934 | Schicht |
| 2,509,984 A | 5/1950 | Morrow |

(Continued)

FOREIGN PATENT DOCUMENTS

| CN | 1059662 A | 3/1992 |
| CN | 1732887 A | 2/2006 |

(Continued)

OTHER PUBLICATIONS

Agnese et al., "Investigating the Influence of Various Plasticizers on the Properties of Isolated Films of Polyvinyl Acetat". The 37th Annual meeting and Exposition of the Controlled Release Society, Jul. 2010, Portland, OR U.S.A.

(Continued)

*Primary Examiner* — Sean C. Barron
(74) *Attorney, Agent, or Firm* — Knobbe, Martens, Olson & Bear, LLP (57) ABSTRACT

The invention describes a methodology for production of a secondary extra-particle fungal matrix for application as a mycological material, manufactured via a Type II actively aerated static packed-bed bioreactor. A pre-conditioned air stream is passed through a substrate of discrete elements inoculated with a filamentous fungus to form an isotropic inter-particle hyphal matrix between the discrete elements. Continued feeding of the air through the substrate of discrete elements and isotropic inter-particle hyphal matrixes develops an extra-particle hyphal matrix that extends from an isotropic inter-particle hyphal matrix in the direction of airflow into a void space within the vessel.

11 Claims, 6 Drawing Sheets

(51) Int. Cl.
　　　*C12P 1/02*　　　(2006.01)
　　　*A01H 15/00*　　　(2006.01)
　　　*C12N 1/14*　　　(2006.01)
　　　*A01G 18/00*　　　(2018.01)

(56) References Cited

U.S. PATENT DOCUMENTS

| | | |
|---|---|---|
| 2,657,647 A | 11/1953 | Rapisarda |
| 2,723,493 A | 11/1955 | Stoller |
| 2,815,621 A | 12/1957 | Carter |
| 2,964,070 A | 12/1960 | Linhardt |
| 3,268,606 A | 8/1966 | Jaeger |
| 3,316,592 A | 5/1967 | Forrest |
| 3,317,375 A | 5/1967 | Molinet et al. |
| 3,421,554 A | 1/1969 | Carter |
| 3,477,558 A | 11/1969 | Fleischauer |
| 3,499,261 A | 3/1970 | Hullhorst et al. |
| 3,708,952 A | 1/1973 | Schulze et al. |
| 3,717,953 A | 2/1973 | Kuhn et al. |
| 3,782,033 A | 1/1974 | Hickerson |
| 3,810,327 A | 5/1974 | Giansante |
| 3,828,470 A | 8/1974 | Stoller |
| 3,961,938 A | 6/1976 | Iizuka et al. |
| 4,027,427 A | 6/1977 | Stoller et al. |
| 4,036,122 A | 7/1977 | Langen |
| 4,038,807 A | 8/1977 | Beardsley et al. |
| 4,063,383 A | 12/1977 | Green |
| 4,073,956 A | 2/1978 | Yates |
| 4,127,965 A | 12/1978 | Mee |
| 4,136,767 A | 1/1979 | Sarovich |
| 4,226,330 A | 10/1980 | Butler |
| 4,263,744 A | 4/1981 | Stoller |
| 4,265,915 A | 5/1981 | MacLennan et al. |
| 4,294,929 A | 10/1981 | Solomons et al. |
| 4,337,594 A | 7/1982 | Hanacek et al. |
| 4,370,159 A | 1/1983 | Holtz |
| 4,568,520 A | 2/1986 | Ackermann et al. |
| 4,620,826 A | 11/1986 | Rubio et al. |
| 4,716,712 A | 1/1988 | Gill |
| 4,722,159 A | 2/1988 | Watanabe et al. |
| 4,878,312 A | 11/1989 | Shimizu |
| 4,922,650 A | 5/1990 | Akao et al. |
| 4,960,413 A | 10/1990 | Sagar et al. |
| 5,021,350 A | 6/1991 | Jung et al. |
| 5,030,425 A | 7/1991 | Bowers-Irons et al. |
| 5,074,959 A | 12/1991 | Yamanaka et al. |
| 5,085,998 A * | 2/1992 | Lebron ............... C02F 3/1231 435/262.5 |
| 5,088,860 A | 2/1992 | Stockdale et al. |
| 5,123,203 A | 6/1992 | Hiromoto |
| 5,230,430 A | 7/1993 | Kidder |
| 5,306,550 A | 4/1994 | Nishiyama et al. |
| 5,335,770 A | 8/1994 | Baker et al. |
| 5,370,714 A | 12/1994 | Ogawa |
| 5,433,061 A | 7/1995 | Hutchinson et al. |
| 5,440,860 A | 8/1995 | Meli et al. |
| 5,475,479 A | 12/1995 | Hatakeyama et al. |
| 5,498,384 A | 3/1996 | Volk et al. |
| 5,503,647 A | 4/1996 | Dahlberg et al. |
| 5,511,358 A | 4/1996 | Morita et al. |
| 5,532,217 A | 7/1996 | Silver et al. |
| 5,569,426 A | 10/1996 | Le Blanc |
| 5,589,390 A | 12/1996 | Higuchi et al. |
| 5,590,489 A | 1/1997 | Hattori et al. |
| 5,598,876 A | 2/1997 | Zanini et al. |
| 5,606,836 A | 3/1997 | Insalaco et al. |
| 5,647,180 A | 7/1997 | Billings et al. |
| 5,681,738 A | 10/1997 | Beelman et al. |
| 5,682,929 A | 11/1997 | Maginot et al. |
| 5,685,124 A | 11/1997 | Jandl |
| 5,711,353 A | 1/1998 | Ichikawa et al. |
| 5,802,763 A | 9/1998 | Milstein |
| 5,854,056 A | 12/1998 | Dschida |
| 5,888,803 A | 3/1999 | Starkey |
| 5,897,887 A | 4/1999 | Haeberli |
| 5,919,507 A | 6/1999 | Beelman et al. |
| 5,944,928 A | 8/1999 | Seidner |
| 5,948,674 A | 9/1999 | Mankiewicz |
| 5,979,109 A | 11/1999 | Sartor et al. |
| 6,041,544 A | 3/2000 | Kananen et al. |
| 6,041,835 A | 3/2000 | Price |
| 6,098,677 A | 8/2000 | Wegman et al. |
| 6,112,504 A | 9/2000 | McGregor et al. |
| 6,197,573 B1 * | 3/2001 | Suryanarayan ........ C12M 21/16 435/286.7 |
| 6,226,962 B1 | 5/2001 | Eason et al. |
| 6,300,315 B1 | 10/2001 | Liu |
| 6,306,921 B1 | 10/2001 | Al Ghatta et al. |
| 6,329,185 B1 | 12/2001 | Kofod et al. |
| 6,349,988 B1 | 2/2002 | Foster et al. |
| 6,402,953 B1 | 6/2002 | Gorovoj et al. |
| 6,425,714 B1 | 7/2002 | Waddell |
| 6,444,437 B1 | 9/2002 | Sporleder et al. |
| 6,471,993 B1 | 10/2002 | Shastri et al. |
| 6,475,811 B1 | 11/2002 | Babcock |
| 6,482,942 B1 | 11/2002 | Vittori |
| 6,491,480 B2 | 12/2002 | Waddell |
| 6,500,476 B1 | 12/2002 | Martin et al. |
| 6,523,721 B1 | 2/2003 | Nomoto et al. |
| 6,603,054 B2 | 8/2003 | Chen et al. |
| 6,620,614 B1 | 9/2003 | Luth et al. |
| 6,660,164 B1 | 12/2003 | Stover |
| 6,679,301 B2 | 1/2004 | Makino et al. |
| 6,726,911 B1 | 4/2004 | Jülich et al. |
| 7,043,874 B2 | 5/2006 | Wasser et al. |
| 7,073,306 B1 | 7/2006 | Hagaman |
| 7,122,176 B2 | 10/2006 | Stamets |
| 7,179,356 B2 | 2/2007 | Aksay et al. |
| 7,395,643 B2 | 7/2008 | Franchini et al. |
| 7,514,248 B2 | 4/2009 | Gower et al. |
| 7,573,031 B2 | 8/2009 | Behar et al. |
| 7,621,300 B2 | 11/2009 | Bonney et al. |
| 7,661,248 B2 | 2/2010 | Conti et al. |
| 7,754,653 B2 | 7/2010 | Hintz |
| 7,836,921 B2 | 11/2010 | Isomura et al. |
| 8,001,719 B2 | 8/2011 | Bayer et al. |
| 8,205,646 B2 | 6/2012 | Isomura et al. |
| 8,227,224 B2 | 7/2012 | Kalisz et al. |
| 8,227,233 B2 | 7/2012 | Kalisz et al. |
| 8,241,415 B2 | 8/2012 | Wantling et al. |
| 8,298,810 B2 | 10/2012 | Rocco et al. |
| 8,313,939 B2 | 11/2012 | Kalisz et al. |
| 8,517,064 B2 | 8/2013 | Isomura et al. |
| 8,658,407 B2 | 2/2014 | Lyons et al. |
| 8,763,653 B2 | 7/2014 | Weigel et al. |
| 8,999,687 B2 | 4/2015 | Bayer et al. |
| 9,079,978 B2 | 7/2015 | Räsänen et al. |
| 9,085,763 B2 | 7/2015 | Winiski et al. |
| 9,253,889 B2 | 2/2016 | Bayer et al. |
| 9,332,779 B2 | 5/2016 | Marga |
| 9,394,512 B2 | 7/2016 | Bayer et al. |
| 9,469,838 B2 | 10/2016 | Schaak et al. |
| 9,485,917 B2 | 11/2016 | Bayer et al. |
| 9,555,395 B2 | 1/2017 | Araldi et al. |
| 9,714,180 B2 | 7/2017 | McIntyre et al. |
| 9,752,122 B2 | 9/2017 | Marga et al. |
| 9,795,088 B2 | 10/2017 | Bayer et al. |
| 9,801,345 B2 | 10/2017 | Bayer et al. |
| 9,803,171 B2 | 10/2017 | Bayer et al. |
| 9,879,219 B2 | 1/2018 | McIntyre et al. |
| 9,914,906 B2 | 3/2018 | Winiski et al. |
| 10,125,347 B2 | 11/2018 | Winiski |
| 10,144,149 B2 | 12/2018 | Araldi et al. |
| 10,154,627 B2 | 12/2018 | McIntyre et al. |
| 10,172,301 B2 | 1/2019 | McNamara et al. |
| 10,266,695 B2 | 4/2019 | Lucht et al. |
| 10,407,675 B2 | 9/2019 | Bayer et al. |
| 10,525,662 B2 | 1/2020 | Bayer et al. |
| 10,537,070 B2 | 1/2020 | Betts et al. |
| 10,583,626 B2 | 3/2020 | Bayer et al. |
| 10,589,489 B2 | 3/2020 | Bayer et al. |
| 10,687,482 B2 | 6/2020 | Ross et al. |
| 10,785,925 B2 | 9/2020 | McNamara et al. |
| 2001/0012235 A1 | 8/2001 | Schuchardt |

(56) References Cited

U.S. PATENT DOCUMENTS

| | | |
|---|---|---|
| 2002/0110427 A1 | 8/2002 | Waddell |
| 2002/0131828 A1 | 9/2002 | Waddell |
| 2002/0131933 A1 | 9/2002 | Delmotte |
| 2003/0017565 A1 | 1/2003 | Echigo et al. |
| 2003/0056451 A1 | 3/2003 | Pisek et al. |
| 2003/0121201 A1 | 7/2003 | Dahlberg et al. |
| 2003/0232895 A1 | 12/2003 | Omidian et al. |
| 2004/0000090 A1 | 1/2004 | Miller |
| 2004/0020553 A1 | 2/2004 | Amano |
| 2004/0166576 A1 | 8/2004 | Sadaie |
| 2004/0177585 A1 | 9/2004 | Vermette |
| 2005/0133536 A1 | 6/2005 | Kelsey et al. |
| 2005/0137272 A1 | 6/2005 | Gaserod et al. |
| 2006/0134265 A1 | 6/2006 | Beukes |
| 2006/0280753 A1 | 12/2006 | McNeary |
| 2007/0079944 A1 | 4/2007 | Amidon et al. |
| 2007/0196509 A1 | 8/2007 | Riman et al. |
| 2007/0225328 A1 | 9/2007 | Fritz et al. |
| 2007/0227063 A1 | 10/2007 | Dale et al. |
| 2007/0294939 A1 | 12/2007 | Spear et al. |
| 2008/0017272 A1 | 1/2008 | Isomura et al. |
| 2008/0046277 A1 | 2/2008 | Stamets |
| 2008/0047966 A1 | 2/2008 | Carson |
| 2008/0145577 A1 | 6/2008 | Bayer et al. |
| 2008/0234210 A1 | 9/2008 | Rijn et al. |
| 2008/0295399 A1 | 12/2008 | Kawai et al. |
| 2008/0296295 A1 | 12/2008 | Kords et al. |
| 2009/0107040 A1 | 4/2009 | Vandnhove |
| 2009/0191289 A1 | 7/2009 | Lutz et al. |
| 2009/0241623 A1 | 10/2009 | Matano et al. |
| 2009/0246467 A1 | 10/2009 | Delantar |
| 2009/0272758 A1 | 11/2009 | Karwacki et al. |
| 2009/0307969 A1 | 12/2009 | Bayer et al. |
| 2009/0321975 A1 | 12/2009 | Schlummer |
| 2010/0101190 A1 | 4/2010 | Dillon |
| 2010/0158976 A1 | 6/2010 | O'Brien et al. |
| 2010/0159509 A1 | 6/2010 | Xu et al. |
| 2010/0199601 A1 | 8/2010 | Boldrini et al. |
| 2010/0227931 A1 | 9/2010 | Kuwano et al. |
| 2010/0243135 A1 | 9/2010 | Pepper et al. |
| 2010/0326564 A1 | 12/2010 | Isomura et al. |
| 2011/0094154 A1 | 4/2011 | Joaquin |
| 2011/0108158 A1 | 5/2011 | Huwiler et al. |
| 2011/0265688 A1 | 11/2011 | Kalisz et al. |
| 2011/0268980 A1 | 11/2011 | Kalisz et al. |
| 2011/0269209 A1 | 11/2011 | Rocco et al. |
| 2011/0269214 A1 | 11/2011 | Kalisz et al. |
| 2011/0306107 A1 | 12/2011 | Kalisz et al. |
| 2012/0000165 A1 | 1/2012 | Williams |
| 2012/0006446 A1 | 1/2012 | Isomura et al. |
| 2012/0060446 A1 | 3/2012 | Merz |
| 2012/0076895 A1 | 3/2012 | Kirejevas et al. |
| 2012/0115199 A1 | 5/2012 | Li et al. |
| 2012/0132314 A1 | 5/2012 | Weigel et al. |
| 2012/0135504 A1 | 5/2012 | Ross |
| 2012/0225471 A1 | 9/2012 | McIntyre et al. |
| 2012/0227899 A1 | 9/2012 | McIntyre et al. |
| 2012/0231140 A1 | 9/2012 | Hofmann et al. |
| 2012/0270031 A1 | 10/2012 | Guan et al. |
| 2012/0270302 A1 | 10/2012 | Bayer et al. |
| 2012/0315687 A1 | 12/2012 | Bayer et al. |
| 2013/0095560 A1 | 4/2013 | McIntyre et al. |
| 2013/0105036 A1 | 5/2013 | Smith et al. |
| 2013/0210327 A1 | 8/2013 | Corominas |
| 2013/0224840 A1 | 8/2013 | Bayer et al. |
| 2013/0274892 A1 | 10/2013 | Lelkes et al. |
| 2013/0309755 A1 | 11/2013 | McIntyre et al. |
| 2014/0038619 A1 | 2/2014 | Moulsley |
| 2014/0056653 A1 | 2/2014 | Scully et al. |
| 2014/0069004 A1 | 3/2014 | Bayer et al. |
| 2014/0093618 A1 | 4/2014 | Forgacs et al. |
| 2014/0163142 A1 | 6/2014 | Zhang et al. |
| 2014/0173977 A1 | 6/2014 | Juscius |
| 2014/0186927 A1 | 7/2014 | Winiski et al. |
| 2014/0371352 A1 | 12/2014 | Dantin et al. |
| 2015/0033620 A1 | 2/2015 | Greetham et al. |
| 2015/0038619 A1 | 2/2015 | McIntyre et al. |
| 2015/0101509 A1 | 4/2015 | McIntyre et al. |
| 2015/0197358 A1 | 7/2015 | Larsen |
| 2015/0342138 A1 | 12/2015 | Bayer et al. |
| 2015/0342224 A1 | 12/2015 | Medoff |
| 2016/0002589 A1 | 1/2016 | Winiski |
| 2016/0264926 A1 | 9/2016 | Winiski et al. |
| 2016/0355779 A1 | 12/2016 | Ross |
| 2017/0000040 A1 | 1/2017 | Bayer et al. |
| 2017/0028600 A1 | 2/2017 | McIntyre et al. |
| 2017/0071214 A1 | 3/2017 | Rehage |
| 2017/0218327 A1 | 8/2017 | Amstislavski et al. |
| 2017/0253849 A1 | 9/2017 | Miller et al. |
| 2017/0253852 A1 | 9/2017 | Bayer et al. |
| 2018/0014468 A1 | 1/2018 | Ross et al. |
| 2018/0148682 A1 | 5/2018 | Ross et al. |
| 2018/0282529 A1 | 10/2018 | Kaplan-Bie |
| 2018/0368337 A1 | 12/2018 | McIntyre et al. |
| 2019/0059431 A1 | 2/2019 | Kozubal et al. |
| 2019/0090436 A1 | 3/2019 | Betts et al. |
| 2019/0284307 A1 | 9/2019 | Chase et al. |
| 2019/0322997 A1 | 10/2019 | Schaak |
| 2019/0330668 A1 | 10/2019 | Kozubal et al. |
| 2019/0338240 A1 | 11/2019 | Carlton et al. |
| 2019/0357454 A1 | 11/2019 | Mueller et al. |
| 2019/0359931 A1 | 11/2019 | Mueller et al. |
| 2019/0390156 A1 | 12/2019 | Bayer et al. |
| 2020/0024577 A1 | 1/2020 | Carlton et al. |
| 2020/0025672 A1 | 1/2020 | Scullin et al. |
| 2020/0055274 A1 | 2/2020 | Bayer et al. |
| 2020/0095535 A1 | 3/2020 | Kozubal et al. |
| 2020/0146224 A1 | 5/2020 | Kaplan-Bie et al. |
| 2020/0157506 A1 | 5/2020 | Bayer et al. |
| 2020/0208097 A1 | 7/2020 | Winiski |
| 2020/0239830 A1 | 7/2020 | O'Brien et al. |
| 2020/0268031 A1 | 8/2020 | Macur et al. |
| 2020/0270559 A1 | 8/2020 | Macur et al. |
| 2020/0392341 A1 | 12/2020 | Smith et al. |
| 2021/0127601 A9 | 5/2021 | Kaplan-Bie et al. |
| 2021/0317433 A9 | 10/2021 | Schaak |
| 2021/0348117 A9 | 11/2021 | Winiski |

FOREIGN PATENT DOCUMENTS

| | | |
|---|---|---|
| CN | 101248869 A | 8/2008 |
| CN | 101653081 A | 2/2010 |
| CN | 106947702 A | 7/2017 |
| EP | 0226292 A1 | 6/1987 |
| EP | 1312547 A1 | 5/2003 |
| EP | 2677030 A1 | 12/2013 |
| EP | 2735318 A1 | 5/2014 |
| EP | 2875805 A1 | 5/2015 |
| EP | 2878340 A1 | 6/2015 |
| EP | 2485779 B1 | 2/2018 |
| EP | 3292769 A1 | 3/2018 |
| GB | 142800 A | 1/1921 |
| GB | 1525484 A | 9/1978 |
| GB | 2032456 A | 5/1980 |
| GB | 2165865 A | 4/1986 |
| IN | 358266 B | 7/2020 |
| JP | H03234889 A | 10/1991 |
| JP | H049316 A | 1/1992 |
| JP | 6111510 B1 | 4/2017 |
| KR | 20050001175 A | 1/2005 |
| KR | 101851655 B1 | 4/2018 |
| WO | WO 1999/024555 | 5/1999 |
| WO | WO 2001/087045 | 11/2001 |
| WO | WO 2005/067977 | 7/2005 |
| WO | WO 2008/025122 | 3/2008 |
| WO | WO 2008/073489 | 6/2008 |
| WO | WO 2010/005476 | 1/2010 |
| WO | WO 2012/122092 | 9/2012 |
| WO | WO 2014/039938 | 3/2014 |
| WO | WO 2014/195641 | 12/2014 |
| WO | WO 2016/149002 | 9/2016 |
| WO | WO 2017/056059 | 4/2017 |
| WO | WO 2017/120342 | 7/2017 |
| WO | WO 2017/136950 | 8/2017 |

(56) References Cited

FOREIGN PATENT DOCUMENTS

| | | |
|---|---|---|
| WO | WO 2017/151684 | 9/2017 |
| WO | WO 2017/205750 | 11/2017 |
| WO | WO 2018/011805 | 1/2018 |
| WO | WO 2018/014004 | 1/2018 |
| WO | WO 2018/064968 | 4/2018 |
| WO | WO 2018/183735 | 10/2018 |
| WO | WO 2018/189738 | 10/2018 |
| WO | WO 2019/046480 | 3/2019 |
| WO | WO 2019/099474 | 5/2019 |
| WO | WO 2019/178406 | 9/2019 |
| WO | WO 2019/217175 | 11/2019 |
| WO | WO 2019/226823 | 11/2019 |
| WO | WO 2019/246636 | 12/2019 |
| WO | WO 2020/023450 | 1/2020 |
| WO | WO 2020/072140 | 4/2020 |
| WO | WO 2020/082043 | 4/2020 |
| WO | WO 2020/082044 | 4/2020 |
| WO | WO 2020/102552 | 5/2020 |
| WO | WO 2020/106743 | 5/2020 |
| WO | WO 2020/176758 | 9/2020 |
| WO | WO 2020/186068 | 9/2020 |
| WO | WO 2020/186169 | 9/2020 |
| WO | WO 2020/237201 | 11/2020 |

OTHER PUBLICATIONS

Amsellem et al., "Long-term preservation of viable mycelia of two mycoherbicidal organisms". Crop Protection (1999) 18: 643-649.

Angelini et al., "Effect of antimicrobial activity of Melaleuca alternifolia essential oil on antagonistic potential of *Pleurotus* species against Trichoderma harzianum in dual culture." World J Microbiol Biotech. (2008) 24(2): 197-202.

Antón et al., "PimM, a PAS Domain Positive Regulator of Pimaricin Biosynthesis in Streptomyces natalensis." Microbiol. (2007) 153: 3174-3183.

Appels et al., "Hydrophobin gene deletion and environmental growth conditions impact mechanical properties of mycelium by affecting the density of the material." Scientific Reports (2018) 8(1): 1-7.

Arshad et al., "Tissue engineering approaches to develop cultured meat from cells: a mini review." Cogent Food & Agriculture (2017) 3(1): 1320814 in 11 pages.

Ashiuchi et al., "Isolation of Bacillus subtilis (chungkookjang), a poly-gamma-glutamate producer with high genetic competence". Appl Microbiol Biotechnol. (2011) 57: 764-769.

Bajaj et al., "Poly (glutamic acid)—An emerging biopolymer of commercial interest". Bioresource Tech. (2011) 102(10): 5551-5561.

Baysal et al., "Cultivation of oyster mushroom on waste paper with some added supplementary materials". Biosource Technology (2003) 89: 95-97.

Begum et al., "Bioconversion and saccharification of some lignocellulosic wastes by Aspergillus oryzae ITCC-4857.01 for fermentable sugar production". Elect J Biotech. (2011) (14)5: 3 in 8 pages.

Belardinelli et al., "Actions of Adenosine and Isoproterenol on Isolated Mammalian Ventricular Myocytes." Circulation Res. (1983) 53(3): 287-297.

Belay et al., "Preparation and Characterization of Graphene-agar and Graphene Oxide-agar Composites." JOAPS (2017) 134(33): 45085.

Binder et al., "Phylogenetic and phylogenomic overview of the Polyporales". Mycologia (Nov.-Dec. 2013) 105(6): 1350-1373.

Blanchette et al., "Fungal mycelial mats used as textile by indigenous people of North America", Mycologia (Feb. 20, 2021) pp. 1-7.

Booth et al., "Potential of a dried mycelium formulation of an indigenous strain of Metarhizium anisopliae against subterranean pests of cranberry." Biocontrol Science and Technology (2000) 10: 659-668.

Bormann et al., "Characterization of a Novel, Antifungal, Chitin-binding Protein from Streptomyces Tendae Tü901 that Interferes with Growth Polarity." J Bacter. (1999) 181(24): 7421-7429.

Bowman et al., "The structure and synthesis of the fungal cell wall". Bioassays (2006) 28(8): 799-808.

Bružauskaite et al., "Scaffolds and Cells for Tissue Regernation: Different Scaffold Pore Sizes—Different Cell Effects." Cytotechnology (2016) 68(3): 355-369.

Byrd, "Clean meat's path to your dinner plate", The Good Food Institute, website accessed Nov. 14, 2018, https://www.gfi.org/clean-meats-path-to-commercialization; 11 pages.

Cerimi et al., "Fungi as source for new bio-based materials: a patent review", Fungal Biol Biotechnol. (2019) 6: 17; 10 pgs.

Chai et al., "β-Glucan Synthase Gene Overexpression and β-Glucans Overproduction in Pleurotus ostreatus Using Promoter Swapping". PLoS ONE (2013) 8(4): e61693 in 7 pages.

Chaudhary et al., "Understanding rice hull ash as fillers in polymers: a review". Silicon Chemistry (2002) 1:281-289.

Chi et al., "Can Co-culturing of Two White-rot Fungi Increase Lignin Degradation and the Production of Lignin-degrading Enzymes?" Inter'l Biodeter Biodegrad. (2007) 59(1): 32-39.

Collins English Dictionary, "Mould", retrieved from http://collinsdictionary.com/dictionary/english/mould, archived on Apr. 8, 2015, 3 pages.

Dias et al., "Synthesis and characterization of chitosan-polyvinyl alcohol-bioactive glass hybrid membranes". Biomatter (2011) 1(1): 114-119.

Elleuche et. al., "Carbonic anhydrases in fungi". Microbiology (2010) 156: 23-29.

Elsacker et al., "Growing living and multifunctional mycelium composites for large-scale formwork applications using robotic abrasive wire-cutting", Construction Bldg Mater. (2021) 283: 122732 in 16 pages.

Fleet G.H., "Cell walls", in The Yeasts, by Rose et al. [Eds.] 2nd Edition. vol. 4. London: Academic Press. (1991) pp. 199-277.

Frandsen R.J.N., "A guide to binary vectors and strategies for targeted genome modification in fungi using Agrobacterium tumefaciens-mediated transformation". J Microbiol Methods (2011) 87: 247-262.

Gardening KnowHow, Perlite Soil Info: Learn About Perlite Potting Soil, online at www.gardeningknowhow.com/garden-how-to/soil-fertilizers/perlite-potting-soil.htm downloaded on Dec. 16, 2015., 3 pages.

Glowacki et al., "Bioconjugation of Hydrogen-bonded Organic Semiconductors with Functional Proteins." J Mate Chem. C (2015) 3(25): 6554-6564.

Goodell et al., "Fungal Decay of Wood: Soft Rot-Brown Rot-white Rot". In Development of Commercial Wood Preservatives; Schultz et al. [Ed.] ACS Symposium Series; American Chemical Society, Washington, D.C. (2008), Chapter 2, pp. 9-31.

Google Report, Complete colonization substrate mushroom (2 pages) Jan. 30, 2018., 2 pages.

Google Dictionary Definition "Composite", downloaded on Nov. 21, 2018; 1 page.

Gourmet Mushroom, Inc., "What is Mushroom?"—Mushroom Facts Mushroom Information—Educational & Science Projects (2004). Downloaded from www.gmushrooms.com, on Nov. 27, 2017; 5 pages.

Grant, James. J.—"An investigation of the airflow in mushroom growing structures, the development of an improved, three-dimensional solution technique for fluid flow and its evaluation for the modelling of mushroom growing structures", Doctoral Thesis Sep. 2002; 326 pages.

Greetham et al., "Pheotypic characterisation of Saccharomyces sensu stricto to Inhibitory Compounds Released During the Deconstruction of Lignocellulosic Material." 3th International Congress on Yeasts, ICY 2012, Aug. 26-30, Madison, USA; 1 page.

Griffin et al., "Regulation of macromolecular synthesis, colony development and specific growth rate of Achlya bisexualis during balanced growth". J General Microbiol. (1974) 80(2): 381-388.

Growers Supply. "Horticultural Coarse Perlite—4 Cubic Fee—Growers Supply". URL: https://growerssupply.com; Growers Sup- (56) References Cited

OTHER PUBLICATIONS ply 2012; www.growerssupply.com/farm/supplies/prod1:gs_growing_mediums:pg111049.html; downloaded Dec. 14, 2020 in 3 pages.

Haneef et al., "Advanced Materials from Fungal Mycelium: Fabrication and Tuning of Physical Properties", Scientific Reports 7(1): 1-11; DOI: 10.1038/srep41292, Jan. 24, 2017.

Heinzkill et al., "Characterization of laccases and peroxidases from wood-rotting fungi (family Coprinaceae)." Appl Environ Microbiol. (1998) 64: 1601-1606.

Heisig et al., USGS, "Ground-Water Resources of the Clifton Park Area, Saratoga County, New York", 2002, retrieved from the internet (Oct. 15, 2016): http://ny.water.usgs.gov/pubs/wri/wri014104/wrir01-4104.pdf; 27 pages.

Home Depot "Miracle Gro® Perlite Mix", retrieved from the internet: http://homedepot.com/p/Miracle-Gro-8-pt-Perlite-Mix-74278430/204502291; 2 pages.

Home Depot "Pennington—Fast Acting Gypsum", retrieved from the internet: http://homedepot.com/p/Miracle-Gro-8-pt-Perlite-Mix-74278430/204502291; 2 pages.

Horton et al., "Regulation of Dikaryon-Expressed Genes by FRT1 in the Basidiomycete Schizophyllum commune". Fungal Genet Biol. (1999) 26(1): 33-47.

Howden et al., "The effects of breathing 5% CO2 on human cardiovascular responses and tolerance to orthostatic stress". Exper. Physiol. (2004) 89(4): 465-471.

Hüttner et al., "Recent advances in the intellectual property landscape of filamentous fungi", Fungal Biol Biotechnol. (2020) 7:16; 17 pgs.

Hyde et al., "The amazing potential of fungi: 50 ways we can exploit fungi industrially". Fungal Diversity (2019) 97(1): 1-136.

Instructables, How to Grow Oyster Mushroom Spawn (Low Tech), retrieved from the internet Aug. 19, 2018: http://www.instructables.com/id/1-How-to-Grow-Oyster-Mushroom-Spawn-Low-Tech/; 17 pages.

Jones et al., "Leather-like material biofabrication using fungi", Nature Sustainability (2020) https://doi.org/10.1038/s41893-020-00606-1, Sep. 7, 2020.

Kamzolkina et al., "Micromorphological features of Pleurotus pulmonarius (Fr.) Quel, and P. ostreaturs (Jacq.) P. Kumm. Strains in pure and binary culture with yeasts". Tsitologiia (2006) 48(2): 153-160.

Kemppainen et al., "Transformation of the Mycorrhizal Fungus Laccaria Bicolor using Agrobacterium tumefaciens." Bioengin Bugs (2011) 2(1): 38-44.

Kerem et al., "Effect of Mananese on Lignin Degradation by Pleurotus ostreatus during Solid-State Fermentation". Applied and Environmental Microbiology (1993) 59(12): 4115-4120.

Kilaru et al., "Investigating dominant selection markers for Coprinopsis cinerea: a carboxin resistance system and re-evaluation of hygromycin and phleomycin resistance vectors". Curr Genet. (2009) 55: 543-550.

Kim et al., "Current Technologies and Related Issues for Mushroom Transformation." Mycobiology (2015) 43(1): 1-8.

Kotlarewski et al., "Mechanical Properties of Papua New Guinea Balsa Wood." European J Wood Wood Products (2016) 74(1): 83-89.

Kück et al., "New tools for the genetic manipulation of filamentous fungi". Appl Microbiol Biotechnol. (2010) 86: 51-62.

Kües, U., "Life History and Development Processes in the Basidiomycete Coprinus Cinereus." Micro Molecular Biol Rev. (2000) 64(2): 316-353.

Kuhar et al., by Ingredi Potassium Sorbate vs Campden Tablets in Wine Making; Jun. 4, 2018. [online]; Retrieved from the Internet <URL: https://ingredi.com/blog/potassium-sorbate-vs-campden-tables-in-wine-making/>; 2 pages.

Kuo, 2005-2006. Glossary of Mycological Terms. Mushroom Expert. Com., pp. 1-13; downloaded from http://www.mushroomexpert.com/glossary.html (May 8, 2015).

Li et al., "Preparation and Characterization of Homogeneous Hydroxyapatite/Chitosan Composite Scaffolds via In-Situ Hydration". J Biomaterials Nanobiotech. (2010) 1: 42-49.

Luo et al., "*Coprinus comatus*: a basidiomycete fungus forms novel spiny structures and infects nematode." Mycologia (2004) 96(6): 1218-1225.

McPherson et al., "Dissolvable Antibiotic Beads in Treatment of Periprosthetic Joint Infection and Revision Arthroplasty: The Use of Synthetic Pure Calcium Sulfate (Stimulan®) Impregnated with Vancomycin & Tobramycin." Reconstructive Review (2013) 3(1) 12 pages.

Merriam-Webster, "Chamber" dictionary definition; https://www.merriam-webster.com/dictionary accessed Jul. 10, 2017; in 4 Pages.

Merriam-Webster, "pack" Thesaurus definition; https://www.merriam-webster.com/thesaurus; synonyms accessed Aug. 19, 2019; in 10 Pages.

Michielse et al., "Agrobacterium-mediated Transformation of the Filamentous Fungus *Aspergillus awamori*." Nature Protocols (2008) 3(10): 1671-1678.

Mitchell et al., [Eds.] "Solid-State Fermentation Bioreactors." Springer Verlag, Berlin/Heidelberg (2006); TOC in 12 Pages.

Moore D., "Fungal Morphogenesis." Cambridge University Press, Cambridge, UK; (1998) TOC in 8 Pages.

Moore D., "Tolerance of Imprecision in Fungal Morphogenesis." In Proceedings of the 4th Meeting on the Genetics and Cellular Biology of Basidiomycetes (Mar. 1998) pp. 13-19.

Mushroom Growers' Handbook 1, "Oyster Mushroom Cultivation". Part II, Chapter 5, (2005) pp. 75-85.

Mushroom Growers' Handbook 2, "Shiitake Bag Cultivation", Part I Shiitake. Published by Mush World (2005) Chapter 4, pp. 73-90 and pp. 105-109.

Naknean et al., "Factors Affecting Retention and Release of Flavor Compounds in Food Carbohydrates." Inter'l Food Res J. (2010) 17(1): 23-34.

Newaz et al., "Characterization of Balsa Wood Mechanical Properties Required for Continuum Damage Mechanics Analysis." Proceedings of the Institution of Mechanical Engineers, Part L: Journal of Materials: Design and Applications (2016) 230(1): 206-218.

Norvell L., Fungi Biology. Encyclopedia.(2002); 2 pages.

Novoselova et al., "Cocultivation of Pleurotus ostreatus (Jacq.) P. Kumm, with yeasts". Moscow University Biol Sciences Bulletin (2011) 66(3): 102-105.

Nussinovitch "Polymer Macro- and Micro-Gel Beads: Fundamentals and Applications", DOI 10.1007/978-1-4419-6618_2, Springer Science & Business Media LLC (2010) TOC in 8 Pages.

Paz et al., "One Step Contruction of Agrobacterium-Recombination-ready-plasmids (OSCAR): An Efficient and Robust Tool for ATMT Based Gene Deletion Construction in Fungi." Fungal Gen Biol. (2011) 48(7): 677-684.

Peksen et al., "Favourable Culture Conditions for mycelial growth of *Hydnum repandum*, a medicinal mushroom." African Journal of Traditional, Complementary and Alternative Medicines (2013) 10(6): 431-434.

Peng et al., "Microbial biodegradation of polyaromatic hydrocarbons". FEMS Microbiol Rev. (2008) 32:927-955.

Perez et al., "Myxococcus xanthus induces actinorhodin overproduction and aerial mycelium formation by Streptomyces coelicolor." Microbial Biotech. (2011) 4(2): 175-183.

Philippoussis et al., "Production of Mushrooms Using Agro-Industrial Residues as Substrates", in Biotechnology for Agro-Industrial Residues, Chapter 9, (2009) pp. 163-187.

Poppe J., Mushroom Growers' Handbook 1, 2004, Part II. Chapter 5, "Substrate", pp. 80-81.

Pompei et al., "The Use of Olive Milling Waste-Water for the Culture of Mushrooms on Perlite". Acta Horticulturae (1994) 361:179-185.

Rai et al., "Production of Edible Fungi", in Fungal Biotechnology in Agricultural, Food, and Environmental Applications, D.K. Arora [Ed.], Marcel Dekker, Inc., (2003), Chapter 21, pp. 383-404.

Ross, P "Pure Culture" 1997-Present; URL: <http://billhoss.phpwebhosting.com/ross/index.php?kind>; downloaded Dec. 14, 2016 in 11 pages.

(56) References Cited

OTHER PUBLICATIONS

Royse et al., "Influence of substrate wood-chip particle size on shiitake (*Lentinula edodes*) yield". Bioresource Tehnology (2001) 76(3): 229-233.
Sapak et al., "Effect of endophytic bacteria on growth and suppression of Tganoderma infection in oil palm". Int J Agric Biol. (2008) 10(2): 127-132.
Schaner et al., "Decellularized Vein as a Potential Scaffold for Vascular Tissue Engineering." J Vascular Surg. (2004) 40(1): 146-153.
Schirp et al., "Production and characterization of natural fiber-reinforced thermoplastic composites using wheat straw modified with the fungus *Pleurotus ostreatus*". J Appl. Polym Sci. (2006) 102: 5191-5201.
Scholtmeijer et al., "Effect of introns and AT-rich sequences on expression of the bacterial hygromycin B resistance gene in the basidiomycete Schizophyllum commune". Appl Environ Microbiol. (2001) 67(1): 481-483.
Schuurman J., "Unique agar Pearls." YouTube video; Feb. 16, 2012, <https://www.youtube.com/watch?v=8GqTTOHETPQ>; 1 page.
Science Daily, May 7, 2007, retrieved from the Internet; http://www.sciencedaily.com/releases/2007/05/070506085628.htm., 3 pages.
Seamon K.B., "Forskolin: Unique Diterpene Activator of Adenylate Cyclase in Membranes and in Intact Cells." PNAS (1981) 78(6): 3363-3367.
Sinotech et al., (2015): retrieved from the Internet http://www.sinotech.com/compressionAndTransferMolding.html., 4 pages.
Slater, M. "Young SoRo Entrepreneur Develops Environmentally Friendly Insulation." The Herald of Randolph. Jun. 21, 2007, pp. 1-2.
Staib et al., "Differential expression of the NRG1 repressor controls species-specific regulation of chlamydospore development in Candida albicans and Candida dubliniensis." Molecular Microbiol. (2005) 55(2): 637-652.
Stamets P., "Mycelium Running". Ten Speed Press (2005); pp. 18, 56, 58, 59, 85, 149, 157, 160 and 291 only.
Stamets P., "Growing Gourmet and Medicinal Mushrooms", (Undated) Chapter 21; p. 363.
Stanev et al., "Open Cell Metallic Porous Materials Obtained Through Space Holders. Part I: Production Methods, A Review". JMSE (2016) 139(5): 21 pages.
Stephens et al., "Bringing Cultured Meat to Market: Technical, Socio-political, and Regulatory Challenges in Cellular Agriculture." Trends in Food Science & Technology (2018) 78: 155-166.
Sundari et al., "Freeze-drying vegetative mycelium of Laccaria fraterna and its subsequent regeneration". Biotechnology Techniques (1999) 13: 491-495.
Tartar et al., "Differential expression of chitin synthase (CHS) and glucan synthase (FKS) genes correlates with the formation of a modified, thinner cell wall in in vivo-produced Beauveria bassiana cells." Mycopathologia (2005) 160(4): 303-314.
Téllez-Jurado et al., "Expression of a heterologous laccase by Aspergillus niger cultured by solid-state and submerged fermentations." Enzyme Microbial Tech. (2006) 38(5): 665-669.
Téllez-Téllez et al., "Growth and laccase production by Pleurotus ostreatus in submerged and solid-state fermentation." Appl Microbiol Biotechnol. (2008) 81(4): 675-679.
Thomas et al., "Growing Orchids in Perlite". In Perlite Plant Guide, The Schundler Company 1951, pp. 1-6, downloaded from http://www.schundler.com/index.html, archived on May 11, 2015.
TimberPress—"How Do Mushrooms Grow So Quickly.", downloaded from the internet: www.timberpress.com/blog/2017/01/how-do-mushrooms-grow-so-quickly, download Feb. 27, 2018 in 7 Pages.
Ugalde U., "Autoregulatory Signals in Mycelial Fungi" in The Mycota: A Comprehensive Treatise on Fungi as Experimental Systems for Basic and Applied Research. K. Esser [Ed.] Springer Publisher, 2nd Edition (2006) Chapter 11; pp. 203-213.
Universal Oil Field, "Sawdust", downloaded from universaloilfield.org on Aug. 23, 2018, 4 pages.
Vara et al., "Cloning and expression of a puromycin N-acetyl transferase gene from Streptomyces alboniger in Streptomyces lividans and *Escherichia coli*". Gene (1985) 33(22): 197-206.
Visser et al., "Pseudoxylaria as stowaway of the fungus-growing termite nest: Interaction asymmetry between Pseudoxylaria, Termitomyces and free-living relatives". Fungal Ecology (2011) 4(5): 322-332.
Volk (2003) "Tom Volk's Fungus of the Month for Oct. 1998". This month's fungus is *Pleurotus ostreatus*; the Oyster mushroom, pp. 1-4, downloaded from http://botit.botany.wise.edu/toms_fungi/oct98.html on May 8, 2015.
Wang et al., "Influence of fungal elicitors on biosynthesis of natamycin by Streptomyces natalensis HW-2". Appl Microbiol Biothechnol. (2003) 97: 5527-5534.
Wikipedia, "Water gel (plain)", Wikipedia Contributors downloaded Aug. 21, 2017 in 1 Page.
Wikipedia, "Wood", downloaded on Nov. 26, 2018, 1 page.
Xiao et al., "A Water-soluble Core Material for Manufacturing Hollow Composite Sections." Comp. Structures (2017) 182: 380-390.
Yang et al., "Medicinal Mushroom *Ganoderma lucidum* as a Potent Elicitor in Production of t-Resveratrol and t-Peceatannol in Peanut Calluses". J Agric Food Chern. (2010) 58(17): 9518-9522.
Zadrazil et al., "Influence of $CO_2$ Concentration on the Mycelium Growth of Three *Pleurotus* Species", European J. Appl. Microbiol., vol. 1, pp. 327-335 (1975).
Zimin et al., "The MaSuRCA genome assembler". Bioinformatics (2013) 29(21): 2669-2677.
International Search Report and Written Opinion for PCT/US2019/047977, dated Nov. 12, 2019.
Bartnicki-Garcia, "Cell wall chemistry, morphogenesis, and taxonomy of fungi", Annual Review Microbiol. (1968) 22(1): 87-108.
Cha et al., "Biomimetic synthesis of ordered silica structures mediated by block copolypeptides". Nature (2000) 403(6767): 289-292.
Dugdale J. "This new surf company is making boards of mushrooms". Blog post—Jun. 25, 2015.
Halseide P., "Cutting brick the safe way". The Aberdeen Group (1988) Publication #M880354 in 2 pages.
Highland Woodworking, "Making Thin Lumber and Veneer Out of Ordinary Boards", Sales Website (2017) in 3 pages.
Holt et al., "Biobased Composition Boards Made from Cotton Gin and Guayule Wastes: Select Physical and Mechanical Properties", Int J Mater Prod Tech. (2009) 36: 104-114.
Islam et al., "Morphology and mechanics of fungal mycelium", Scientific Reports, (2017) 7(1): 1-12.
Kerem et al., "Chemically defined solid-state fermentation of Pleurotus Ostreatus". Enzyme Microbiol Tech. (1993) 15(9): 785-790.
Kokubo et al., "Ca,P-rich layer formed on high-strength bioactive glass-ceramic A-W". J Biomed Mater Res. (1990) 24(3): 331-343.
Koutsoukos et al., "Precipitation of calcium carbonate in aqueous solutions". J Chem Soc., Faraday Trans. 1, Physical Chemistry in Condensed Phases, (1984) 80(5): 1181-1192.
Lu et al., "Theoretical Analysis of Calcium Phosphate precipitation in simulated Body Fluid". Biomaterials (2005) 26(10): 1097-1108—Pre-Pub. Version by Hong Kong University of Science and Technology, Department of Mechanical Engineering, Kowloon; 34 pages.
Molvinger et al., "Porous chitosan-silica hybrid microspheres as a potential catalyst". Chem Mater. (2004) 16(17): 3367-3372.
Monmaturapoj et al., "Influence of preparation method on hydroxyapatite porous scaffolds". Bull Mater Sci. (2011) 34(7): 1733-1737.
Manoli et al., "Crystallization of calcite on chitin". J Cryst Growth, (1997) 182(1-2): 116-124.
Mushroom Source, "Aspen Wood Shavings for Mushroom Cultivation", Website (2015) in 2 pages.
National Institute of Health (NIH/NIBIB), "Tissue Engineering and Regenerative Medicine", Retrieved Sep. 24, 2018 from https://www.nibib.nih.gov/science-education/science-topics/tissue-engineering-and-regenerative-medicine in 13 pages.
Passauer U. et al., "Pilze in Höhlen" [Cave Mushrooms]. Denisia (2016) 37: 211-224.

(56) References Cited

OTHER PUBLICATIONS

Stewart B., "Concrete Fence Posts: Fact Sheet", Texas Agriculture Extension Service, Texas A & M University (1975) Article L-1368 in 4 pages.
Trinci et al., "II. Unrestricted Growth of Fungal Mycelia", The Mycota—Growth, Differenciation and Sexuality by Wessels et al. [Eds], Springer, Berlin, Heidelberg, (1994) Chapter II: 175-193.
Udawatte et al., "Solidification of xonotlite fibers with chitosan by hydrothermal hot pressing". J Mater Sci. Lttrs. (2000) 45(6): 298-301.
University of Sydney, "Competition Between Fungi". Webpage, accessed Jul. 16, 2014—http://bugs.bio.usyd.edu.au/learning/resources/Mycology/Ecology/competition.shtml in 3 pages.
Varma et al., "Porous calcium phosphate coating over phosphorylated chitosan film by a biomimetic method". Biomaterials (1999) 20(9): 879-884.
Wagner A. "Mycelium Biking—Eco-Design at its Best", Master's Thesis at Lulea University of Technology (2016) in 92 pages.
Woller R. "The Pearl Oyster Mushroom", University of Wisconsin Website (2011) in 2 pages.
Wan-Mohtar et al., "The morphology of Ganoderma lucidum mycelium in a repeated-batch fermentation for exopolysaccharide production", Biotechnology Reports (2016) 11: 2-11.
Weaver et al., "The stomatopod dactyl club: a formidable damage-tolerant biological hammer". Science (2012) 336(6086): 1275-1280.
Yamasaki et al., "A hydrothermal hot-pressing method: Apparatus and Application". J Mater Sci Lttrs. (1986) 5(3): 355-356.
Zivanovic et al., "Changes in Mushroom Texture and Cell Wall Composition Affected by Thermal Processing". J Food Service (2004) 69: 44-49.
Abbadi et al., "Immunocytochemical identification and localization of lipase in cells of the mycelium of Penicillium cyclopium variety", Appl Microbial Biotechnol (1995) 42: 923-930.
Ando et al., "Cosmetic material for skin whitening—contains mushroom mycelium cultured matter and e.g. ginseng extract, chondroitin sodium sulphate and/or hyaluronic acid", WPI/THOMSON (Jan. 14, 1992), 1992(8): Accession #1992-062018; Abstract of JP4009316A; in 9 pages.
Antinori et al., "Advanced mycelium materials as potential self-growing biomedical scaffolds." Scientific reports (2021) 11(1): 1-14.
Attias et al., "Biofabrication of Nanocellulose-Mycelium Hybrid Materials", Adv Sustainable Syst. (2020) 5(2): 2000196 in 12 pages; Supporting Information in 7 pages.
Borrás et al., "Trametes versicolor pellets production: Low-cost medium and scale-up", Biochem Eng J. (2008) 42(1): 61-66.
Collins English Dictionary, "Cavity", Definition; retrieved on Nov. 8, 2021; 1 page.
Green et al., "Mechanical Properties of Wood", Forest Products Laboratory, 1999. in Wood Handbook—Wood as an engineering material. Gen Tech. Rep. FPL-GTR-113, Chapter 4 in 46 pages.
Hidayat et al., "Characterization of polylactic acid (PLA)/kenaf composite degradation by immobilized mycelia of Pleurotus ostreatus". Inter Biodeter Biodegrad. (2012) 71: 50-54.
Holt et al. "Fungal mycelium and cotton plant materials in the manufacture of biodegradable molded packaging material: Evaluation study of select blends of cotton byproducts." J Biobased Mater Bioenergy (2012) 6(4): 431-439.
Jiang et al., "Manufacturing of Natural Composites with a Mycelium Binder and Vacuum-infused Vegetable Oil-based Resins", Poster dated May 2014; 1 page.
Jiang et al., "Vacuum Infusion of Mycelium-Bound Biocomposite Preforms with Natural Resins", CAMX ExpoConference Proceedings, Oct. 13-16, 2014, 13 pages.
Jiang et al., "Bioresin Infused then Cured Mycelium-based Sandwich-structure Biocomposites: Resin Transfer Molding (RTM) Process, Flexural Properties, and Simulation." J Cleaner Production (2019) 207: 123-135.
Jones et al., "Mycelim Composites: A Review of Engineering Characteristics and Growth Kinetics", J Bionanoscience (2017) 11(4): 241-257.
Jones et al., "Waste-derived Low-cost Mycelium Composite Construction Materials with Improved Fire Safety", FAM (Fire and Materials) (2018) 42(7): 816-825.
Jones et al., Chitin-chitosan Thin Films from Microbiologically Upcycled Agricultural By-products. In 13th International Conference on the Mechanical Behavious of Materials, Melbourne, Australia (Jun. 2019) p. 66; in 7 pages.
Kuhn et al., [Eds.] Cell Walls and Membranes in Fungi—An Introduction (Abstract) in Biochemistry of Cell Walls and Membranes in Fungi, Chapter 1, Springer Verlag Berlin/Heidelberg 1990, 2 pages.
Merriam-Webster, "desiccated" (Adj.) Definition; downloaded on Nov. 8, 2021; 1 page.
Meyer et al., "Comparison of the Technical Performance of Leather, Artificial Leather, and Trendy Alternatives." Coatings (Feb. 2021) 11(2): 226; 14 pages.
Pathway-27, "Beta-glucan", Aug. 2012, retrieved from http://http://www.pathway27.eu/topstory/beta-glucan/ on Oct. 7, 2021 in 2 pages.
Vetchinkina et al., "Bioreduction of Gold (III) Ions from Hydrogen Tetrachloaurate . . . " Scientific Practical J Health Life Sciences No. 4, ISSN 22188-2268, (2013) pp. 51-56.
Wang et al., "Chemical and structural factors influencing enzymatic saccharification of wood from aspen, birch and spruce". Biomass Bioengin. (2018) 109: 125-134.
Williams, J. "Growth Industry", Financial Times Jan. 12, 2019 (Mogu—Radical by Nature); download from URL <: https://mogu.bio/growth-industry-financial-times-uk-article/> in 1 page.
Wösten et al., "How a fungus escapes the water to grow into the air", Current Biology. (1999) 9(2): 85-88.
Wösten et al., "Growing Fungi Structures in Space", ACT Research Category/Space Architecture; Noordwijk, The Netherlands (Oct. 15, 2018) in 17 pages.
Zeng Z., "Cosmetic composition for cleaning skin, comprises glossy ganoderma spores and collagens, content of glossy ganoderma spores in composition and content of collagens in composition", WPI/Thomson (Feb. 5, 2006) 7: Accession #2007-057767; Abstract of CN1732887A; in 11 pages.
Ziegler et al., "Evaluation of Physico-mechanical Properties of Mycelium Reinforced Green Biocomposites Made from Cellulosic Fibers", Appl Engin Agricult. (2016) 32(6): 931-938.

\* cited by examiner

BIOREACTOR PARADIGM FOR THE PRODUCTION OF SECONDARY EXTRA-PARTICLE HYPHAL MATRICES

This application claims the benefit of U.S. Provisional Patent Application 62/740,159, filed Oct. 2, 2018.

This invention relates to a bioreactor paradigm for the production of secondary extra-particle hyphal matrices. More particularly, this invention relates to an actively aerated packed-bed bioreactor paradigm for the production of secondary extra-particle hyphal matrices. Still more particularly, this invention relates to a method of producing a mycological material.

BACKGROUND OF THE INVENTION

As is known from published US Patent Application 2015/0033620, a mycological biopolymer product consisting entirely of fungal mycelium may be made by inoculating a nutritive substrate with a selected fungus in a sealed environment except for a void space, which space is subsequently filled with a network of fungal mycelium. The environmental conditions for producing the mycological biopolymer product, i.e. a high carbon dioxide ($CO_2$) content i.e. from 5% to 7% by volume and an elevated temperature i.e. from 85° F. to 95° F., prevent full differentiation of the fungus into a mushroom. There are no stipe, cap, or spores produced. The biopolymer product grows into the void space of the tool, filling the space with an undifferentiated mycelium chitin-polymer, which is subsequently extracted from the substrate and dried.

As is also known from pending U.S. patent application Ser. No. 16/190,585, filed Nov. 14, 2018, another method of growing a biopolymer material employs incubation of a growth media comprised of nutritive substrate and a fungus in containers that are placed in a closed incubation chamber with air flows passed over each container while the chamber is maintained with a predetermined environment of humidity, temperature, carbon dioxide and oxygen. The mycological biopolymer is grown into a panel at a dry density of 0.5 to 4 pounds per cubic foot on a dry mass basis.

Filamentous fungi are comprised of cross-linked networks of filamentous cells called hyphae, which expand via polarized tip extension and branch formation (increasing the number of growing tips), which is equivalent to cell division in animals and plants. Hyphal tip extension can display a number of tropisms (positive or negative) including gravitropisms, autotropisms, and galvanotropisms, of which modification is adequate to affect meaningful organizational and morphological variety in the fungal thallus (mycelium) and fruiting bodies (mushrooms).

Filamentous fungi are defined by their phenotypic plasticity and may produce a secondary mycelium which, based on the "fuzzy logic" of differentiation as a function of differential expression of discrete "subroutines" rather than defined pathways, can express variable degrees of differentiation spanning from complex reproductive structures (mushrooms) to a completely undifferentiated vegetative mycelium.

Type I unaerated and unmixed bioreactors represent one of the most commonly used paradigms for solid-state fermentation, which consists of a shallow tray containing solid-substrate and fungal precursor, which is placed in either an active or passively controlled incubation environment where fungal growth is dependent on passive oxygen and heat diffusion between the fungal-particle matrix and the external environment. Within this paradigm, the depth of the tray represents the primary limiting variable affecting oxygen and temperature diffusion.

As described in published US Patent Application 2018/0146627, the expansion and isolation of a secondary extra-particle mycelium from a solid-substrate fermented with filamentous fungi is specifically dependent on Type I tray-based bioreactor systems. In these systems, passive diffusion of respiratory effluent is used to determine the growth environment, within which expansion of the secondary extra-particle mycelium occurs as a function of negatively gravitropic expansion. Within this paradigm, even if the tray is maintained within an actively controlled incubation environment, temperature and gas exchange inputs remain inherently indirect as oxygen and temperature diffusion will remain passive at the interface of the fungal-particle matrix and external environments. Additionally, the environment within the developing extra-particle mycelium is controlled only through diffusion, which becomes an increasing restriction as the thickness and density of the extra-particle mycelium increases. This feedback imposes logical limitations on large scale development of tissue, and may increase morphological heterogeneity.

Type II actively aerated and unmixed bioreactors represent a class of bioreactor defined by a static bed of discrete particles, around and between which microbial fermentation occurs, with air actively introduced from either end of the particle bed with forced diffusion through the particle matrix. This class of bioreactor allows for active heat removal and supply of oxygen through the particle bed, reducing or eliminating bed depth as a significant limiting variable. Further, the air stream can be pre-conditioned to specific temperatures prior to input into the particle bed, allowing for modification of the direct temperature and gas exchange rates experienced by the inter-particle environment during fermentation, and further allowing for specific temporal modification of these variables.

Accordingly, it is an object of the invention to efficiently use a Type II actively aerated static packed-bed bioreactor to manufacture a secondary extra-particle fungal matrix for application as a mycological material.

It is another object of the invention to provide for a greater degree of material morphology and property control in the manufacture of a secondary extra-particle fungal matrix.

It is another object of the invention to simplify the manufacture of a mycological material.

Briefly, the invention provides a method of producing a mycological material employing a Type II actively aerated static packed-bed bioreactor.

The method includes the steps of providing a vessel having a chamber and loading a substrate of discrete elements inoculated with a filamentous fungus into the chamber.

The vessel is characterized in being constructed to contain the loaded substrate in a condition wherein an air stream can be passed through the substrate and out of the vessel. In one embodiment, the vessel may be oriented vertically and the air stream passed vertically through the substrate either upwardly or downwardly. In another embodiment, the vessel may be oriented horizontally, and the air stream passed horizontally through the substrate.

In still another embodiment, the vessel is characterized in being constructed to contain the loaded substrate in vertically or horizontally separated sections with the air stream introduced between the separated sections of substrate to flow through each of the sections.

In operation, after loading of the vessel, a pre-conditioned air stream is fed through the vessel for diffusion between the discrete elements in the chamber and for a time sufficient for the filamentous fungus to expand a contiguous network of hyphae between and around the discrete elements to form an isotropic inter-particle hyphal matrix (IPM).

In accordance with the method, the pre-conditioned air stream continues to be fed through the vessel for diffusion between the discrete elements and the isotropic inter-particle hyphal matrix for a time sufficient to develop a polarized condition within the vessel wherein air exits the isotropic inter-particle hyphal matrix as a laminar flow into at least one void space within the vessel and to form an extra-particle hyphal matrix (EPM) extending from the isotropic inter-particle hyphal matrix in the direction of airflow within the at least one void space.

The discrete elements may be in the form of particles that can support filamentous fungal growth. For example, the particles may be lignocellulose (e.g. agricultural residue, wood) which would act as a nutrient source for the fungus. The particles could be acquired and processed according to typical known processes; for instance harvested from trees and ground to size using a hammer mill Alternatively, the particles may be ones that do not act as a nutrient source for the fungus but only as a solid support for supplemented nutrition and fungal growth (for example, pearlite mixed with water and supplemented nutrients to support fungal growth).

The discrete elements may also be in the form of fibers so long as air can be passed through the fiber matrix and filamentous fungal growth can occur around and between the fibers.

In one embodiment, the vessel has a permeable partition within the vessel to separate the chamber with the loaded inoculated substrate from a void space and the air stream is fed through the vessel to pass downwardly through the chamber into the void space. The vessel should be permeable on the exit end in order to allow the effluent air stream to exit the void space of the vessel. This could be done by perforating the vessel end, through a valve, or any other means of allowing effluent air to escape.

In a second embodiment, the air stream is fed through the vessel to pass upwardly through the chamber with the loaded inoculated substrate into a void space above the loaded chamber.

In a third embodiment, the substrate of discrete elements inoculated with a filamentous fungus is separated into two spaced apart sections within the chamber of the vessel and the pre-conditioned air stream is fed into the vessel between the substrate sections for diffusion between the discrete elements in each section to form an isotropic inter-particle hyphal matrix therein and to form an extra-particle hyphal matrix extending from the isotropic inter-particle hyphal matrix in the direction of airflow.

This latter embodiment produces two separate extra-particle hyphal matrixes; one at one end of the vessel and another at the opposite end of the vessel.

In each embodiment, the vessel may be disposed vertically so that the air stream flows vertically through the inoculated substrate and isotropic inter-particle hyphal matrix or the vessel may be disposed horizontally so that the air stream flows horizontally through the inoculated substrate and isotropic inter-particle hyphal matrix.

In a fifth embodiment, which is applicable to any of the above four embodiments at least one of a paramorphogen (such as terpene or alkyl pyrone), a volatile compound, and other aromatic compounds may be introduced into the air prior to permeation through the substrate particle matrix, IPM, and EPM in order to further modify the specific morphology and density of the EPM.

In a sixth embodiment, which is applicable to any of the above five embodiments, a second low-density substrate, which need not be suitable for supporting IPM on its own, is included in the void space. During manufacture, EPM extends from the inoculated matrix as it would into an open space, but instead grows around and within the low-density second substrate generating a composite of EPM and secondary substrate with modified material properties.

In a seventh embodiment, which is applicable to any of the above six embodiments, the bottom void space is of a defined geometry. During manufacture, EPM 8 expands into the bottom void space creating an EPM of the same geometry as the bottom void space.

Critically, Type I tray bioreactor systems depend on either a homogenized or heterogeneous extra-matrix environment (i.e. external of the particle-fungal matrix) developed as a function of passive respiratory effluent dissipation, with gas exchange and heat diffusion occurring passively at the interface of the extra- and inter-particle matrix environments. Published US Patent Application 2015/0033620 teaches specifically to regulation of $CO_2$ to no less than 3%, with regular exhausting to manage this gas concentration.

Further, the prior art also teaches explicitly to development of a negatively gravitropic secondary extra-particle mycelium, in which expansion only occurs against gravity and into the extra-matrix environment. The extra-matrix environment described in the prior art may require active control of the gas concentration.

The described invention herein leverages a Type II actively aerated bioreactor paradigm in which air and temperature inputs are inherently direct, in that passage of these inputs occurs directly through the substrate particle matrix, IPM, and EPM at a defined volumetric (either constant or dynamic) rate. In this case, under most conditions, the output respiratory effluent would be <3% $CO_2$, directly teaching against Published US Patent Application 2015/0033620.

Filamentous fungi are defined by their phenotypic plasticity, and the temporal development, morphology, cell concentration, efficiency of producing an EPM, and the morphology of the EPM is directly dependent on gas and temperature conditions. Considering this phenotypic plasticity, the direct nature of input conditions (volumetric air exchange rate, air temperature, introduction of paramorphogens/volatile compounds into input air) by the described invention therefore provides for a paradigm for more direct modification of the morphological characteristics of the developed EPM, and thereby the mechanical properties of the EPM, than prior art.

Additionally, conditioning of airflow and gas concentration to a stage in which development of EPM occurs is a direct function of the IPM (diffusion through, as well as respiratory effluent from the IPM, which is modified simply by changing the volumetric air exchange rate and depth of the substrate particle bed), which allows for considerable simplification of the bioreactor design as compared to prior art as the need for elaborate airflow systems and active gas composition control are reduced, thereby enjoying an increase in scalability for commercial manufacture. Within the polarized and direct conditions described, development of the EPM may occur as either positively or negatively gravitropic, but will always occur at the output of respiratory effluent from the substrate particle matrix-IPM as hyphal extension in the direction of air flow.

These and other objects and advantages of the invention will become more apparent from the following detailed description taken in conjunction with the drawings wherein:

Figure 1A:
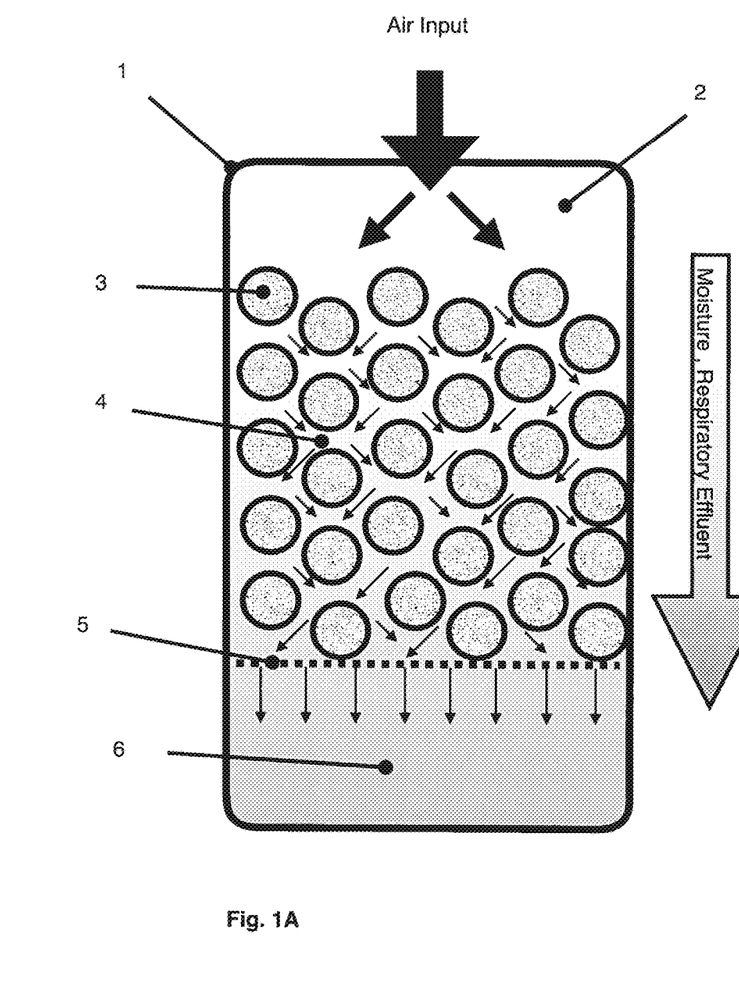
FIG. 1A schematically illustrates the direction and pattern of airflow and respiratory effluent through an inoculated substrate in a vessel in accordance with the method of the invention.

Referring to FIG. 1A, the method of producing a mycological material comprising the steps of providing a vessel 1 having a chamber that can be loaded with a substrate of discrete elements 3 inoculated with a filamentous fungus into the chamber.

As illustrated, the vessel 1 has a head space 2 at the upper end and a permeable partition 5 within the vessel 1 separating the chamber from a void space 6 below the partition 5.

Pre-conditioned air (at near-saturation and a defined temperature and gas composition) is fed into the top of the vessel 1 (or head-space 2) and diffuses down and between the discrete substrate elements 3 as indicated by the arrows 4 with the air flow exiting through the permeable partition 5. In this case, the specific gas composition and volumetric air flow rate may be constant, or may be modulated dynamically.

Figure 1B:
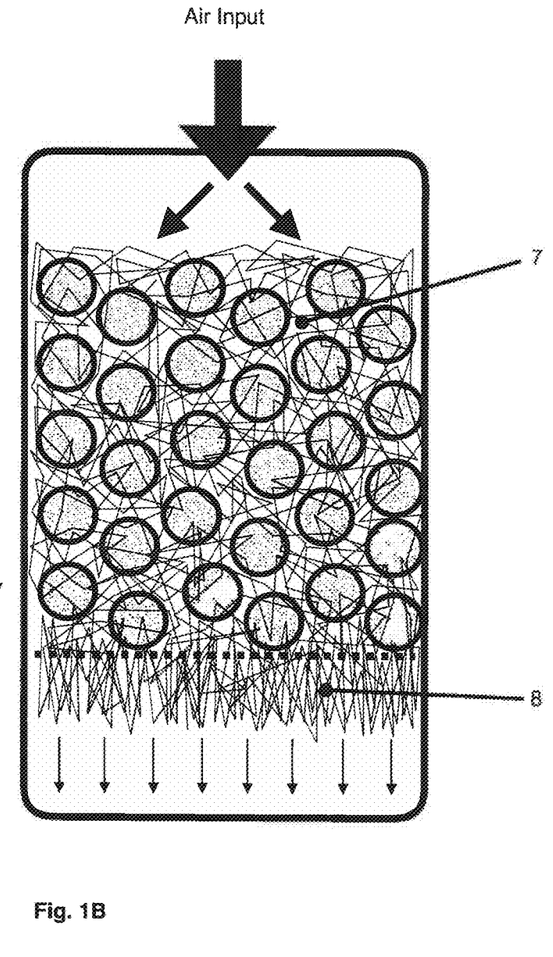
FIG. 1B schematically illustrates the pattern of fungal growth within the inoculated substrate of FIG. 1A in accordance with the method of the invention.

Referring to FIG. 1B, under these conditions, the filamentous fungus expands a contiguous network of filamentous cells (hyphae) between and around the discrete substrate particles 3 forming an isotropic inter-particle hyphal matrix (IPM) 7.

As air diffuses between the particles 3 and through the IPM 7, a polarized condition develops within the vessel 1 in which air exiting the IPM 7 as laminar flow (as a function of the substrate particle matrix-IPM acting as a plenum) into the underlying void space 6 is of higher concentration of moisture than air entering the vessel (due to re-saturation during passage through IPM) and contains respiratory effluent ($CO_2$, VOC, other signaling chemicals). Importantly, this creates a single, vertically oriented gradient of moisture and respiratory effluent (a polarized condition) culminating in the underlying void space 6 experiencing the highest concentrations with even, laminar flow of the air and respiratory effluent. Within this polarized condition, an extra-particle hyphal matrix (EPM) 8 extends from the IPM 7 in a positively gravitropic orientation, extending in the direction of airflow within the bottom void-space 6.

The morphology of EPM 8 is of increased anisotropy as compared to IPM 7 with dominant directionality occurring in the vertical orientation. The EPM 8 is then removed from the permeable partition 5 for utilization as a mycological material per Applications.

The following example is given with respect to FIG. 1A and FIG. 1B.

Example 1. Production of EPM

1. Discrete lignocellulose particles are amended with supplemental nutrition, hydrated to a stage amenable to fungal growth, and combined with the spawn of filamentous fungal species *Ganoderma tsugae* (i.e. preparation of inoculated substrate) to form discrete particles 3 inoculated with a filamentous fungus.
2. Inoculated substrate of inoculated particles 3 are loaded into the bioreactor vessel 1 which contains a permeable partition 5 and which consists of a top head-space 2, a chamber to receive the inoculated substrate matrix, and a bottom void-space 6 below the permeable partition 5.
3. Air is fed into the top (head-space) of the bioreactor vessel at a rate of 0.2 volumes per bioreactor volume per minute, which has been pre-conditioned to an average temperature of 85° F. and a relative humidity (RH) of >90%. This pre-conditioned air diffuses through the inoculated substrate as indicated by the arrows 4 and exits through the permeable partition 5, into the bottom void-space 6, and out of the bioreactor with effluent $CO_2$ concentration of <3%. These input conditions are maintained for the duration of the growth cycle.
4. Fungal growth occurs within the lignocellulose particle matrix by development of an isotropic hyphal matrix between and around the discrete lignocellulose particles (i.e. development of IPM). As growth of IPM progresses, the flow of pre-conditioned air per step 3 continues through the IPM, re-saturating the air to approach 100% RH and evacuating respiratory effluent, creating a top-down gradient of RH and respiratory effluent, and laminar flow from the bottom of the lignocellulose particle matrix-IPM into the bottom void-space 6 and out of the bioreactor.
5. From the IPM, a positively gravitropic extra-particle hyphal matrix (EPM) extends through the permeable partition 5 and into the bottom void-space 6, extending in the direction of airflow. The developed EPM represents a distinct structural morphology from the IPM, with a cell volume density (cell volume per total volume) of 2× that of the IPM, a directional coherency (degree of anisotropy of the hyphal matrix) of 3.2× that of IPM, and oriented hyphal agglomeration (galvanotropism) into strands increasing the average strand thickness to 1.11× that of IPM.
6. EPM is expanded to a target thickness based on the specific application requirements, then separated from the permeable partition 5 for post-processing dictated by the specific application.

Referring to FIG. 2, wherein like reference characters indicate like parts as above, the vessel 1 is constructed so that the pre-conditioned air is fed into the bottom of the vessel 1 and diffuses up and between the discrete substrate elements 3 to form isotropic inter-particle hyphal matrixes (IPM) 7 between the elements 3. In this embodiment, the extra-particle hyphal matrixes (EPM) 8 extends from the IPM 7 in the direction of airflow within the upper void-space 6 and development of the EPM is negatively gravitropic.

The following example is given with respect to FIG. 2.

Figure 2:
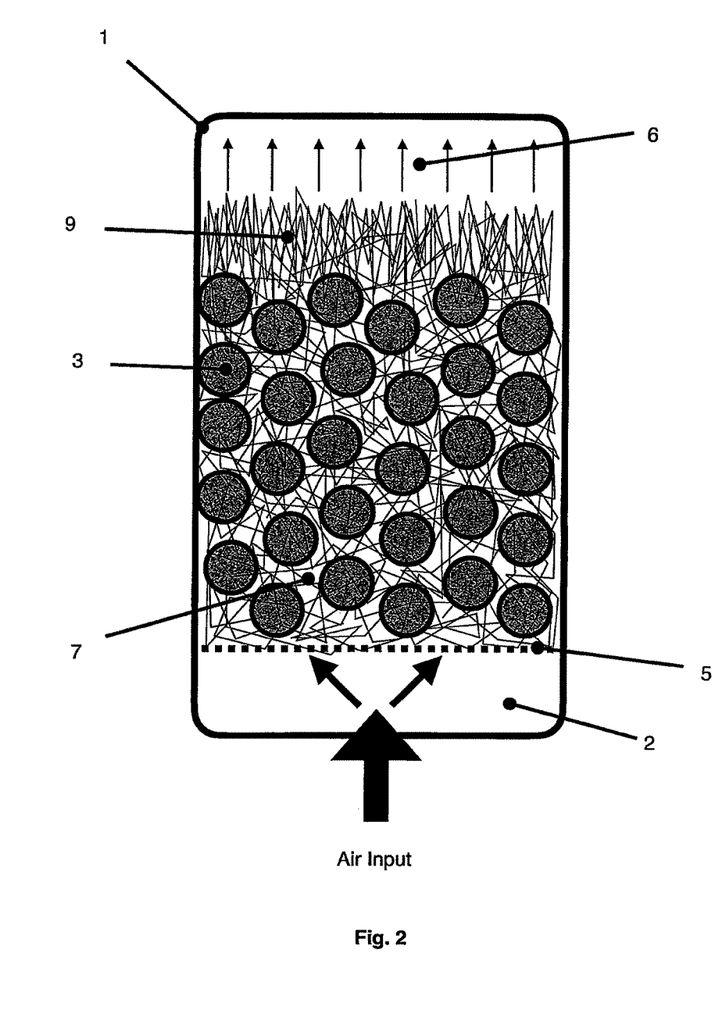
FIG. 2 schematically illustrates an embodiment wherein the direction of airflow is upward through the inoculated substrate.

Example 2. The Procedure of Example 1, Modifying EPM Structural Characteristics by Specific Modification of Input Temperature and Airflow Conditions 1. Example 1 steps 1 and 2.
2. Per Example 2 step 3, with average temperature modified to 90° F., and airflow rate modified to 1.2 volumes per bioreactor volume per minute.
3. Example 1 step 4.
4. Example 1 step 5, with EPM morphology modified to a cell volume density of 4.5× that of IPM, a directional coherency of 2.6× that of IPM, and average hyphal strand thickness of 1.29× that of IPM.
5. Example 1 step 6.

Figure 3:
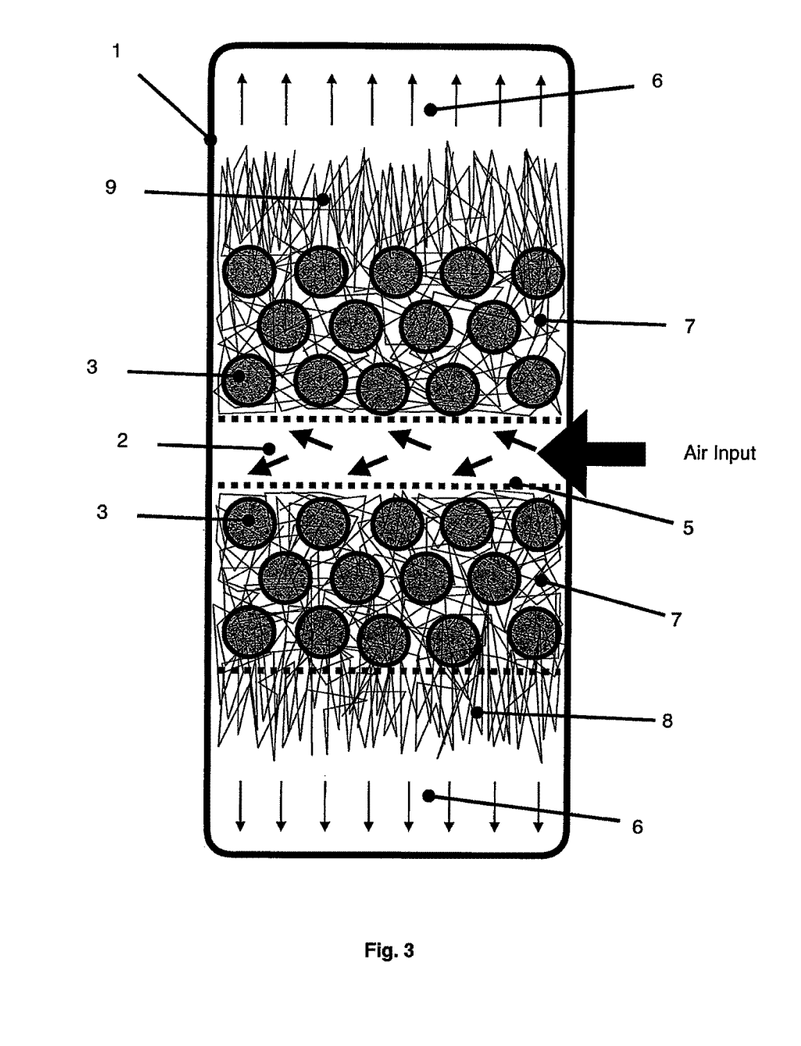
FIG. 3 schematically illustrates an embodiment where the substrate of discrete elements inoculated with a filamentous fungus is separated into two spaced apart sections within the chamber of a vessel and air passed through each section in accordance with the method of the invention.

Referring to FIG. 3, wherein like reference characters indicate like parts as above, the vessel 1 has a pair of permeable partitions 5 at mid-height to form a head space 2 therebetween and a pair of chambers for loading of two separate sections of the substrate of inoculated elements 3 therein.

In operation, air is input into the head-space 2 in the center of the bioreactor vessel 1 defined by the permeable partitions 5, from which air diffuses both down and up through the substrate particle matrix-IPM, in which laminar flow of the respiratory effluent outputs at both the bottom and top of the substrate particle matrix-IPM, where EPM 6 manifests as both positively and negatively gravitropic growth.

The following example is given with respect to FIG. 3.

Example 3. The Procedure of Example 1, Modifying EPM Structural Characteristics by Introduction of an Aromatic Compound into the Input Air 1. Example 1 steps 1 and 2.
2. Example 1 step 3, with terpene introduced into the pre-conditioned air prior to introduction to the inoculated substrate.
3. Example 1 step 4.
4. Example 1 step 5, wherein the EPM and/or IPM is of reduced density and greater directional coherency as a function of the terpene exposure during IPM/EPM development.
5. Example 1 step 6.

Figure 4:
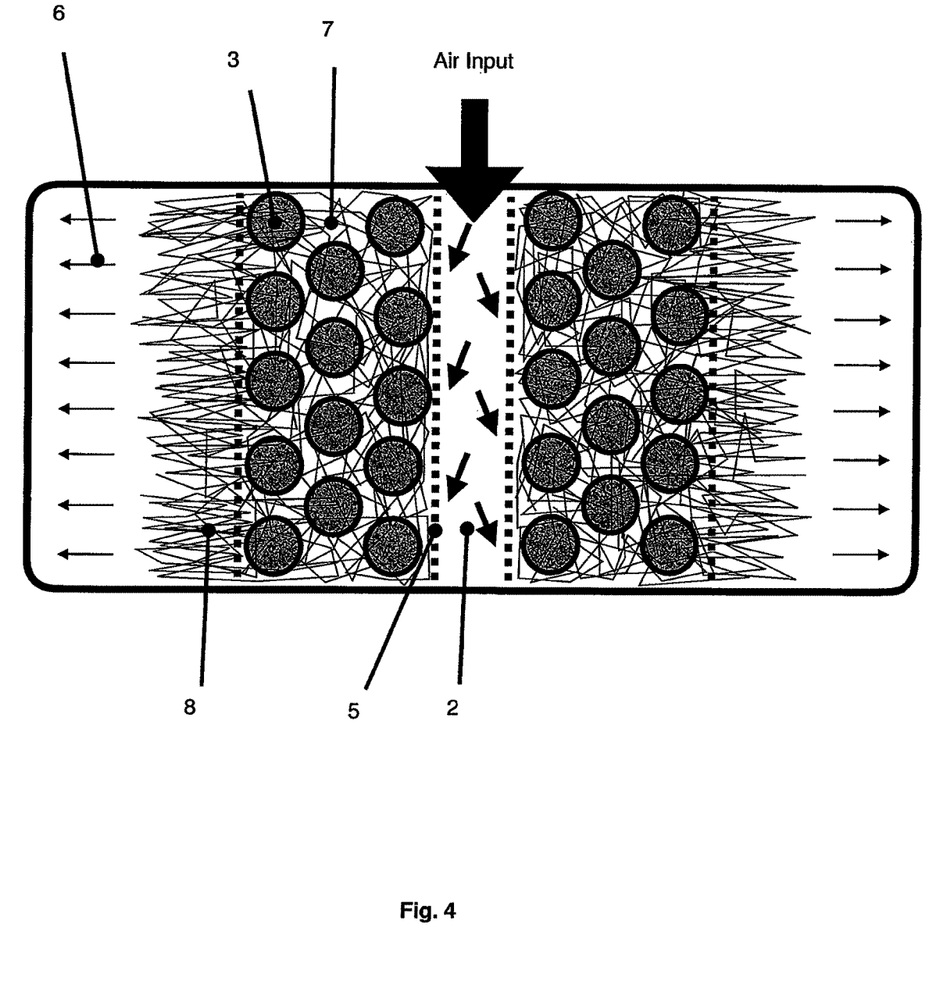
FIG. 4 schematically illustrates a vessel as in FIG. 3 disposed in a horizontal manner in accordance with the invention.

Referring to FIG. 4, wherein like reference characters indicate like parts as above, the orientation of the vessel 1 of FIG. 3 is adjusted so that airflow, the gradient of respiratory effluent, and EPM extension occurs in the horizontal direction rather than the vertical direction.

Figure 5:
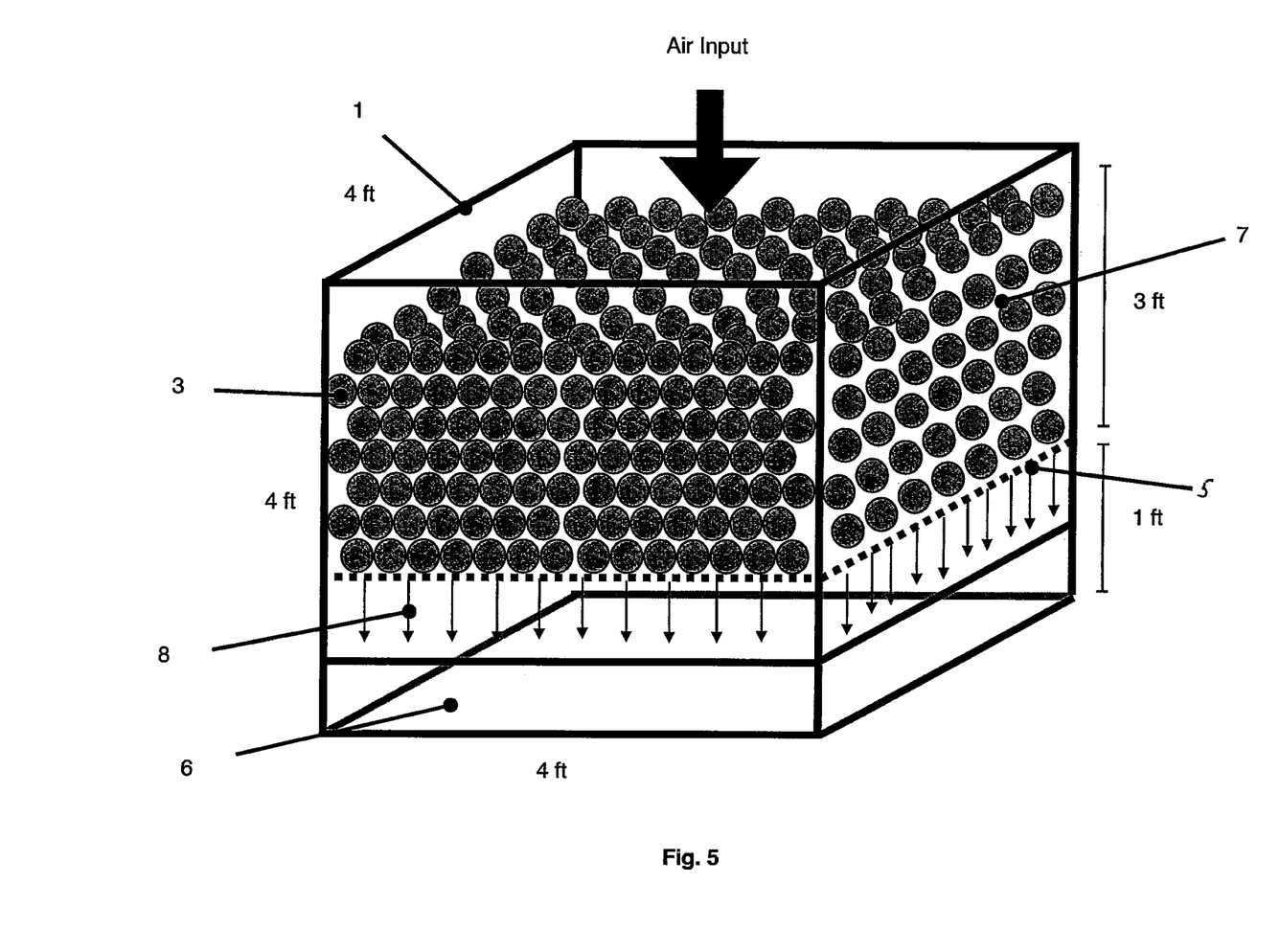
FIG. 5 schematically illustrates a vessel of cubic shape for performing the method of the invention.

Referring to FIG. 5, wherein like reference characters indicate like parts as above, the vessel 1 is a 4×4×4 ft Type II packed-bed actively aerated bioreactor of cubic shape.

The following example is given with respect to FIG. 5.

Example 4. Production of EPM Using a 4×4×4 ft Type II Packed-Bed Actively Aerated Bioreactor 1. The vessel 1 is a 4×4×4 ft container.
2. The permeable partition 5 is placed at a depth of 3 ft, allowing for 1 ft of empty volume 6 below the permeable partition 5.
3. Inoculated substrate elements 3 are loaded in the top 3 ft of the vessel 1.
4. Air is fed into the top (head-space) of the bioreactor vessel and through the particle matrix per Example 1 steps 3. and 4.
5. IPM 7 develops around and between substrate elements 3.
6. EPM 8 extends in a positively gravitropic orientation into the bottom void space 6 to a given target thickness, e.g. a thickness of up to 12 inches as a function of incubation time.
7. EPM is separated from the permeable partition 5 and post-processed per Example 1 step 6.

Figure 6:
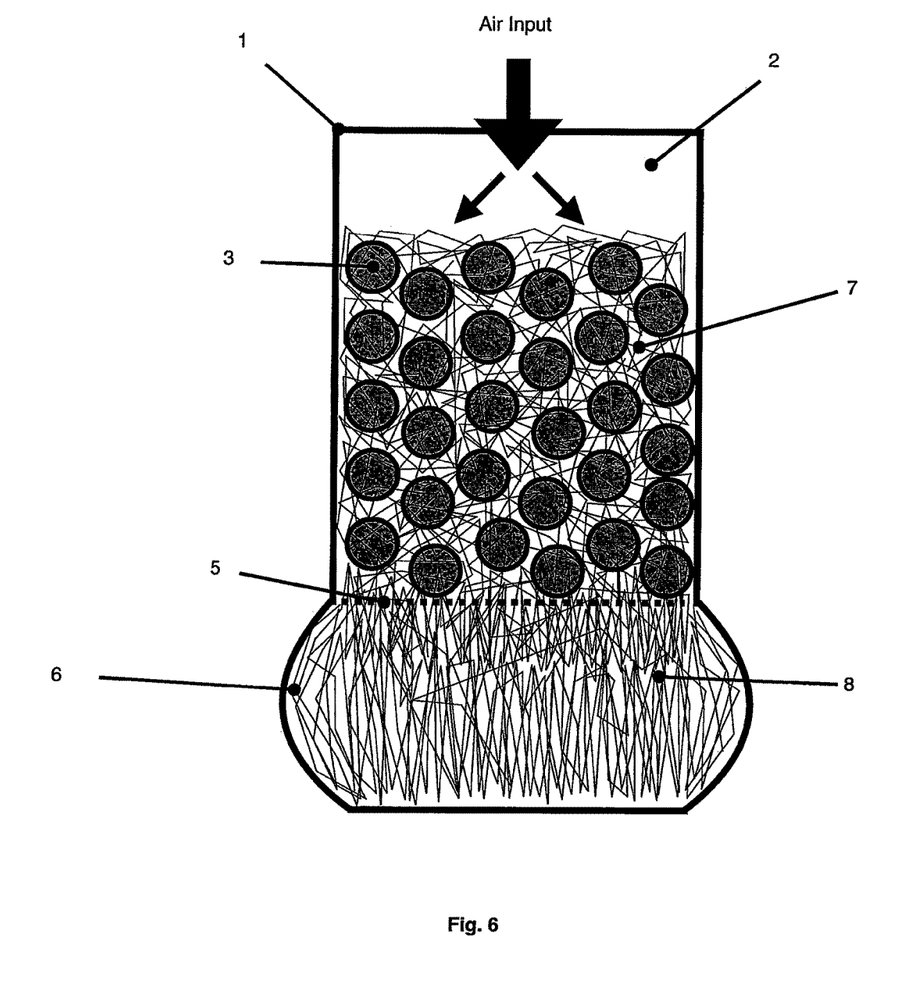
FIG. 6 schematically illustrates a vessel as in FIG. 1A with bottom void space of a defined geometry in accordance with the invention.

Referring to FIG. 6, wherein like reference characters indicate like parts as above, the vessel 1 may be made with a base that defines a void space 6 of a selected geometric shape, for example, of an oval cross-sectional shape.

In operation, EPM 8 expands in a positively gravitropic orientation into the bottom void space 6, producing an EPM of a defined geometry.

Alternatively, a vessel 1 with a base that defines a void space 6 of a selected geometric shape may have a second low-density substrate positioned in the void space 6 and, during operation, the extra-particle hyphal matrix is allowed to grow around and within the second low-density substrate to form a composite of the extra-particle hyphal matrix and the second low-density substrate.

Example 5. Expansion of EPM into a Secondary Substrate to Form an EPM-Secondary Substrate Composite 1. Example 1 step 1.
2. A secondary substrate consisting of a low-density cotton fiber is loaded into the bottom void-space 6 of the vessel 1 below the permeable partition 5.
3. Example 1 steps 2-4.
4. Example 1 step 5, wherein the developing EPM extends through and around the cotton fiber substrate creating a composite EPM-cotton fiber material with a higher tensile strength than the mycelium EPM alone or cotton fiber individually.
5. EPM is expanded to a target thickness depending on the depth of the void space 6 so as to envelope the cotton fiber adequately, then is separated from the permeable bottom for post-processing as dictated by the specific application.

The invention thus provides a method of producing a mycological material, i.e. a secondary extra-particle fungal matrix, in a simple inexpensive manner. Further, the invention provides a paradigm to efficiently use a Type II actively aerated static packed-bed bioreactor to manufacture a secondary extra-particle fungal matrix for application as a mycological material.

The invention provides a paradigm for production of secondary extra-particle hyphal matrices (EPM) as:

A mycological material for replacement of petroleum-based low-density foams, such as polyurethane foams. The simplified paradigm described here, as compared to the prior art, provides an opportunity for direct modification of density and morphological characteristics of the EPM, increases the potential scalability of manufacture and material range of fungal EPM, increasing competitiveness with petroleum-based foams.

A cellular scaffolding, for example the growth of mammalian cells within the EPM. The described invention is a paradigm for allowing for specific modification of EPM density and morphological characteristics by modification of the direct temperature and gas exchange inputs. This may be applied to producing EPM specifically intended for providing a scaffold for mammalian cells for applications such as whole-cut meat substitutes and biomedical applications. For example, EPM porosity and density may be specifically modified for impregnation of mammalian cells of a given size, or the degree of hyphal agglomeration into cords and directional coherency of the hyphal cords may be modified to mimic vessels or vasculature.

What is claimed is:

1. A method of producing a mycological material comprising the steps of
providing a vessel having a chamber;
loading a substrate of discrete elements inoculated with a filamentous fungus into said chamber;
feeding a pre-conditioned air stream through said vessel for diffusion between said discrete elements in said chamber and for a time sufficient for said filamentous fungus to expand a contiguous network of hyphae between and around said discrete elements to form an isotropic inter-particle hyphal matrix; and
continuing to feed said pre-conditioned air stream through said vessel for diffusion between said discrete elements and said isotropic inter-particle hyphal matrix for a time sufficient to develop a polarized condition within said vessel wherein air exits said isotropic inter-particle hyphal matrix as a laminar flow into at least one void space within said vessel and to form an extra-particle hyphal matrix extending from said isotropic inter-particle hyphal matrix in the direction of airflow within said at least void space.

2. A method as set forth in claim 1 wherein said vessel has a permeable partition within said vessel separating said chamber from said void space and said air stream is fed through said vessel passing downwardly through said chamber into said void space.

3. A method as set forth in claim 1 wherein said air stream is fed through said vessel passing upwardly through said chamber into said void space.

4. A method as set forth in claim 1 wherein said step of loading includes separating said substrate of discrete elements inoculated with a filamentous fungus into two spaced apart sections within said chamber.

5. A method as set forth in claim 4 wherein said pre-conditioned air stream is fed through said vessel for diffusion between said discrete elements in each said section to form an isotropic inter-particle hyphal matrix therein and to form an extra-particle hyphal matrix extending from said isotropic inter-particle hyphal matrix in the direction of airflow.

6. A method as set forth in claim 1 wherein said vessel is disposed vertically and said air stream flows vertically through each said section.

7. A method as set forth in claim 1 wherein said vessel is disposed horizontally and said air stream flows horizontally through each said section.

8. A method as set forth in claim 1 further comprising the step of introducing at least one of a paramorphogen, a volatile compound and an aromatic compound into said pre-conditioned air stream prior to diffusion between said discrete elements to modify the specific morphology and density of said extra-particle hyphal matrix.

9. A method as set forth in claim 1 further comprising the steps positioning a a second low-density substrate in said at least one void space within said vessel and allowing said extra-particle hyphal matrix to grow around and within said second low-density substrate to form a composite of said extra-particle hyphal matrix and said second low-density substrate.

10. A method as set forth in claim 9 wherein said at least one void space has a selected geometric shape and said composite forms into said shape.

11. A method as set forth in claim 1 wherein said at least one void space has a selected geometric shape and said extra-particle hyphal matrix forms into said shape.

* * * * *